United States Patent
Blanchard et al.

(10) Patent No.: US 12,343,146 B2
(45) Date of Patent: Jul. 1, 2025

(54) PROBE ADVANCEMENT DEVICE AND RELATED SYSTEMS AND METHODS

(71) Applicant: Becton, Dickinson and Company, Franklin Lakes, NJ (US)

(72) Inventors: Curtis H. Blanchard, Riverton, UT (US); Adam J. Boud, Bluffdale, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 787 days.

(21) Appl. No.: 17/570,554

(22) Filed: Jan. 7, 2022

(65) Prior Publication Data

US 2022/0218252 A1    Jul. 14, 2022

Related U.S. Application Data

(60) Provisional application No. 63/135,377, filed on Jan. 8, 2021.

(51) Int. Cl.
*A61M 39/10*    (2006.01)
*A61B 5/15*    (2006.01)
*A61M 39/12*    (2006.01)

(52) U.S. Cl.
CPC ....... *A61B 5/150992* (2013.01); *A61M 39/12* (2013.01); *A61M 2039/1077* (2013.01)

(58) Field of Classification Search
CPC ............ A61B 5/150992; A61M 39/12; A61M 2039/1077
USPC ........................................................ 600/581
See application file for complete search history.

(56) References Cited

U.S. PATENT DOCUMENTS

| | | | | |
|---|---|---|---|---|
| 3,335,723 A | * | 8/1967 | Waldman, Jr. | A61M 25/06 D24/117 |
| 3,825,001 A | * | 7/1974 | Bennet | A61M 25/0111 604/170.02 |
| 5,715,815 A | | 2/1998 | Lorenzen et al. | |
| 5,944,695 A | * | 8/1999 | Johnson | A61M 25/0637 604/164.11 |
| 5,984,908 A | * | 11/1999 | Davis | A61M 25/0043 604/524 |
| 10,076,272 B2 | * | 9/2018 | Devgon | A61M 39/1011 |
| 10,143,411 B2 | * | 12/2018 | Cabot | A61B 5/150236 |
| 10,525,274 B2 | * | 1/2020 | Tseng | A61B 18/245 |
| 11,969,247 B2 | | 4/2024 | Burkholz et al. | |

(Continued)

FOREIGN PATENT DOCUMENTS

| | | | |
|---|---|---|---|
| WO | 2019018473 A2 | 1/2019 | |
| WO | 2019018479 A1 | 1/2019 | |

*Primary Examiner* — Etsub D Berhanu
*Assistant Examiner* — Nelson Alexander Glover
(74) *Attorney, Agent, or Firm* — The Webb Law Firm

(57) ABSTRACT

A probe advancement device may be configured to couple to a catheter assembly. The probe advancement device may include a flexible housing, which may include a proximal end and a distal end. The probe advancement device may include a probe advancement element coupled to the proximal end of the flexible housing. The probe advancement element may include a probe extending in a distal direction within the flexible housing. The flexible housing may be configured to collapse along an axis in response to the probe being advanced in the distal direction. The probe may include a tube for blood collection, a guidewire, or another suitable element.

19 Claims, 9 Drawing Sheets

(56) References Cited

U.S. PATENT DOCUMENTS

| | | |
|---|---|---|
| 2006/0074398 A1 | 4/2006 | Whiting et al. |
| 2008/0319387 A1* | 12/2008 | Amisar .............. A61M 25/0111 604/533 |
| 2016/0316988 A1 | 11/2016 | Balz et al. |
| 2016/0316998 A1 | 11/2016 | Lombardi |
| 2019/0151622 A1 | 5/2019 | Seidenberger |
| 2020/0023166 A1 | 1/2020 | Burkholz et al. |
| 2020/0316346 A1 | 10/2020 | Burkholz et al. |
| 2022/0001161 A1 | 1/2022 | Burkholz et al. |

\* cited by examiner

PROBE ADVANCEMENT DEVICE AND RELATED SYSTEMS AND METHODS

CROSS-REFERENCE TO RELATED APPLICATION

This application claims priority to U.S. Provisional Application No. 63/135,377, filed Jan. 8, 2021, which is hereby incorporated by reference in its entirety.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of a catheter assembly that includes the catheter. After placement of the needle has been confirmed, the clinician may remove the needle, leaving the catheter in place for future blood withdrawal or fluid infusion.

Catheters typically provide an access port by which other devices may obtain access to the catheter while the catheter is positioned in a patient's vasculature. These other devices may be employed to perform various tasks such as obtaining a blood sample, injecting a fluid, performing a measurement, monitoring, etc. In many instances, the catheter of an IV catheter device may become occluded (e.g., due to a thrombus or fibrin sheath) which may prevent the performance of such tasks. If the catheter has become occluded, a clinician may attempt to remove the occlusion such as by inserting a needle, wire, or other structure through the catheter. However, removing an occlusion using currently available techniques is not always effective, is oftentimes difficult to perform, and may cause trauma to the vasculature of the patient.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to probe advancement devices to facilitate advancement of a probe within a catheter, as well as related systems and methods. In some embodiments, a probe advancement device may be employed to perform various tasks, including obtaining a blood sample. In many instances, the catheter of an IV catheter device may become occluded (e.g., due to a thrombus or fibrin sheath) which may prevent a successful blood draw. In some embodiments, the probe may be advanced by the probe advancement device to remove or provide a pathway through an occlusion.

In some embodiments, a probe advancement device may be configured to couple to a catheter assembly. In some embodiments, the probe advancement device may include a flexible housing, which may include a proximal end and a distal end. In some embodiments, a probe advancement element may be coupled to the proximal end of the flexible housing. In some embodiments, the probe advancement element may include a probe extending in a distal direction within the flexible housing. In some embodiments, the flexible housing may be configured to collapse along an axis in response to the probe being advanced in the distal direction.

In some embodiments, the probe may include one of a guidewire and a tube. In some embodiments, a proximal end of the probe advancement element may be configured to couple to a blood collection device.

In some embodiments, the probe advancement device may include a support element disposed within the flexible housing. In some embodiments, a distal end of the support element comprises a male luer and a proximal end of the support element comprises a female luer. In some embodiments, the probe may extend through the support element.

In some embodiments, the probe advancement device may include multiple support elements spaced apart within the flexible housing. In some embodiments, the probe may extend through the support elements. In some embodiments, a distal end of each of the support elements may include a male luer and a proximal end of each of the support elements may include a female luer. In some embodiments, each of the support elements may be configured to lock on the probe.

In some embodiments, an end connector may be disposed at a distal end of the flexible housing and another connector may be disposed at a proximal end of the flexible housing. In some embodiments, in response to the probe being advanced in the distal direction and collapse of the flexible housing, the end connector may be configured to couple to the other connector. In some embodiments, the end connector may include a female luer adapter and the other connector may include a male luer adapter.

In some embodiments, the probe advancement device may include an alignment rod disposed within the flexible housing to maintain alignment between the probe advancement element and the end connector. In some embodiments, at least a portion of the flexible housing may be transparent such that the probe is visible through the flexible housing.

In some embodiments, the probe advancement device may include a biasing member disposed within the flexible housing between the probe advancement element and the distal end of the flexible housing. In some embodiments, the biasing member may be configured to bias the probe in a retracted position. In some embodiments, the probe advancement element may be configured to compress the biasing member in a distal direction to collapse the flexible housing along the axis in response to the probe being advanced in the distal direction.

In some embodiments, the probe advancement device may include a near access grip element disposed within the flexible housing towards the distal end of the flexible housing. In some embodiments, the near access grip element may be configured to manipulate a position of the probe within the flexible housing. In some embodiments, the near access grip element may include a first end and a second end configured to be resiliently pinched together such that the probe is retained therebetween. In some embodiments, the near access grip element may be configured to be selectively translated along or parallel to the axis within the flexible housing.

In some embodiments, a probe advancement system may include the blood collection device, the flexible housing, and the probe advancement element. In some embodiments, a fluid pathway may extend through the flexible housing and/or into the blood collection device. In some embodiments, the probe advancement system may include the catheter assembly, which may be coupled to the distal end of the flexible housing and in fluid communication with the fluid pathway. In some embodiments, the catheter assembly may be configured to receive the probe therethrough.

In some embodiments, the fluid pathway may extend around the probe and/or between the probe and an inner surface of the flexible housing. In these embodiments, the fluid pathway may be configured to collapse along an axis of the flexible housing in response to the probe being advanced in the distal direction. In some embodiments, the probe may include a tube, and the fluid pathway may extend through the tube. In some embodiments, the proximal end of the flexible housing may include the other connector. In some embodiments, the other connector may include a shaft and the tube may extend distally from the shaft. In some embodiments, the distal end of the flexible housing may include the end connector, and the shaft may be configured to insert into the end connector to form a fluid-tight seal.

In some embodiments, a method to advance the probe for a blood draw may include coupling the probe advancement device to the catheter assembly. In some embodiments, the catheter assembly may include a catheter adapter, which may include a proximal end, a distal end, and a lumen extending therethrough. In some embodiments, the catheter assembly may include a catheter extending from the distal end of the catheter adapter and which may be intravenous. In some embodiments, the method may include coupling a blood collection device to the probe advancement device. In some embodiments, the probe may be advanced in a distal direction to create a fluid pathway through the catheter assembly. In some embodiments, after the probe is advanced in the distal direction, the blood collection device may be actuated to collect blood from a patient via the fluid pathway.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE DRAWINGS

Example embodiments will be described and explained with additional specificity and detail through the use of the accompanying drawings in which.

DESCRIPTION OF EMBODIMENTS

In the specification and the claims, the term "catheter assembly" should be construed as any device that includes an IV catheter. The term "probe advancement device" should be construed as any device that is configured to advance and/or retract a probe within an IV catheter. In some embodiments, a probe advancement device may be a separate device from a catheter assembly with which the probe advancement device may be used. In other embodiments, a probe advancement device may include a catheter assembly or may be monolithically formed with the catheter assembly as a single unit.

Figure 1A:
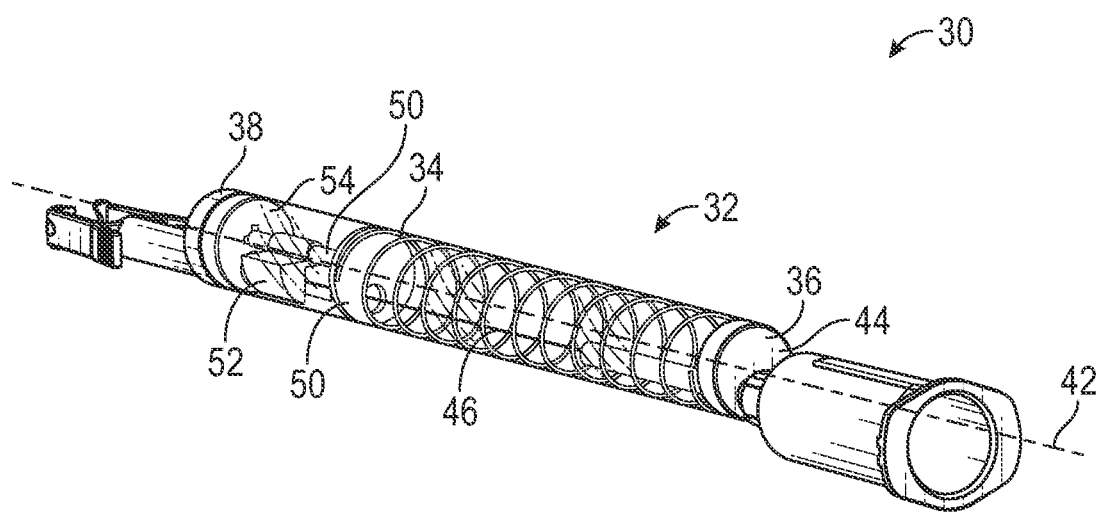
FIG. 1A is a perspective view of an example probe advancement device, in accordance with some embodiments.
Figure 1B:
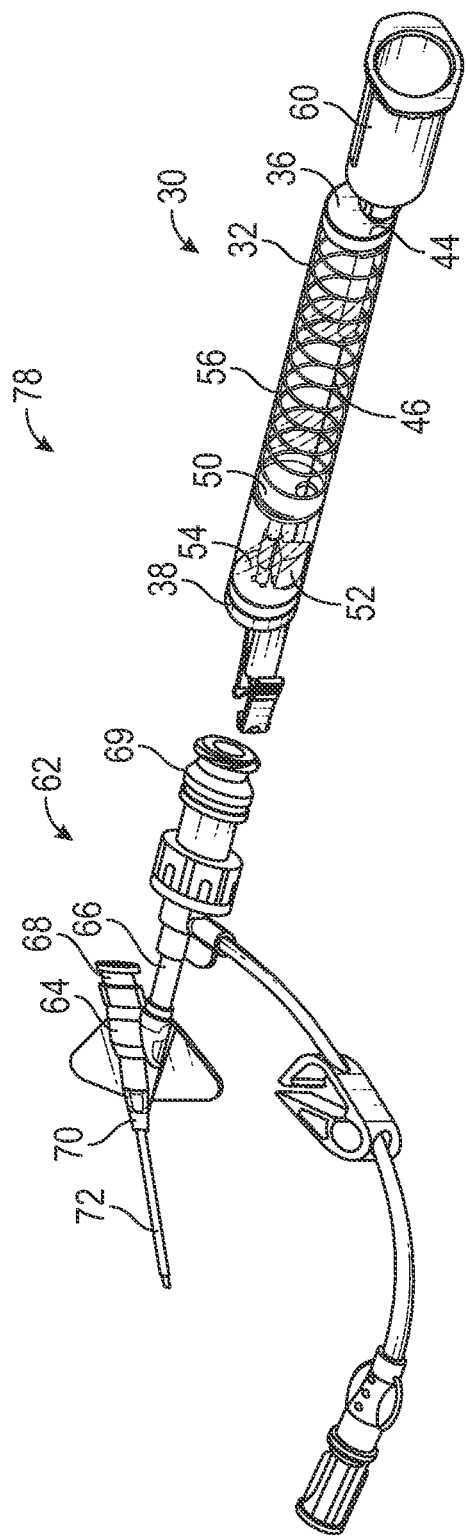
FIG. 1B is an upper perspective view of an example probe advancement system in accordance with some embodiments.

FIGS. 1A and 1B illustrate a probe advancement device 30 for advancing a probe 46 within a catheter 72. In some embodiments, the probe 46 may include a tube through which blood may flow. In other embodiments, the probe 46 may include a guidewire, such as, for example, a nickel titanium guidewire.

Various embodiments of the probe advancement device 30 may be employed to perform various tasks, including obtaining a blood sample, for example. For example, in some embodiments, the probe advancement device 30 may deliver a probe 46 through a catheter assembly 62 to clear a portion of a catheter 72 that has become occluded (e.g., due to a thrombus or fibrin sheath). Failing to clear such an occlusion may prevent a successful blood draw. Some embodiments presented herein may shorten an effective length of the buckling column of the probe 46 and/or reduce drag as the probe 46 is advanced distally.

Referring now to FIG. 1A, in a first set of example embodiments, the probe advancement device 30 may include a flexible housing 32 having a proximal end 36 and a distal end 38. In some embodiments, the flexible housing 32 may include a flexible biocompatible plastic material or other suitable flexible medical-grade polymer, such as, for example, one or more of the following: polyethylene, PEEK, polycarbonate, polyetherimide, polysulfone, polypropylene, and polyurethane. In some embodiments, the flexible housing 32 may include a transparent material to facilitate visualization of obstructions and/or advancement of a probe 46 therein. In some embodiments, the flexible housing 32 may include an accordion-like structure forming a collapsible lumen or fluid pathway. In some embodiments, the flexible housing 32 may be aligned with an axis 42. In some embodiments, the axis 42 may include a central or longitudinal axis of the flexible housing 32, which may extend through the proximal end 36 and the distal end 38.

In some embodiments, a probe advancement element 44 may be coupled to the proximal end of the flexible housing 32. In some embodiments, the probe advancement element 44 may include a rigid or resilient material. In some embodiments, the probe advancement element 44 may include a shape substantially matching a cross-sectional profile of the flexible housing 32. As illustrated, for example, the flexible housing 32 may form a cylinder while the probe advancement element 44 may form a circle having a diameter substantially matching a diameter of the cylinder. In this manner, in some embodiments, the probe advancement element 44 may substantially occlude the proximal end 36 of the flexible housing 32. In some embodiments, the probe advancement element 44 may include any suitable shape to substantially occlude the proximal end 36 of the flexible housing 32.

In some embodiments, the proximal end 36 of the probe advancement device 30 may include a luer adapter or other coupling feature configured to couple to a corresponding luer adapter or coupling feature disposed at the distal end 38. In this manner, in some embodiments, the flexible housing 32 may be compressed or fully compressed by coupling the coupling feature at the proximal end 36 to the corresponding coupling feature at the distal end 38. In some embodiments, the proximal end 36 of the probe advancement device 30 may include a male luer, which may include a shaft 81 configured to couple to a female luer at the distal end 38.

In some embodiments, the probe 46 may extend in a distal direction from the probe advancement element 44 within the flexible housing 32. In some embodiments, the probe 46 may include a guidewire or tube. In some embodiments, the tube may be cylindrical. In some embodiments, the flexible housing 32 may be configured to collapse along the axis 42 when the probe 46 is advanced in the distal direction. For example, in some embodiments, the accordion-like structure of the flexible housing 32 may result in the flexible housing 32 having a length that progressively shortens in response to the probe 46 advancing in the distal direction.

In some embodiments, as discussed in more detail below, the probe advancement device 30 may further include a near access grip element 52. In some embodiments, the near access grip element 52 may be disposed within the flexible housing 32 and/or proximate to the distal end 38. Some embodiments of the near access grip element 52 may be configured to manipulate a position of the probe 46 within the flexible housing 32. In this manner, the probe 46 may advance through part or all of a catheter (see, for example, the catheter 72 in FIG. 1B) to clear obstructions, thereby facilitating blood draw success.

In some embodiments, a seal, such as, for example, an O-seal or other suitable rubber or plastic seal, may be disposed between the probe advancement element 44 and the proximal end 36 of the flexible housing 32. In some embodiments, a luer adapter or other coupling feature may be coupled to or integrated with the probe advancement element 44. In these and other embodiments, the luer adapter or other coupling feature may form a seal at the proximal end 36. In this manner, in some embodiments, the probe 46 may include a guidewire and/or the flexible housing 32 may form an air-tight fluid pathway through which blood can be drawn using a VACUTAINER® LUER-LOK™ Access Device ("LLAD", available from Becton Dickinson & Company of Franklin Lakes, New Jersey), a syringe, or another suitable blood collection device.

In some embodiments, the probe 46 may include a tube, and the tube may extend from the probe advancement element 44. In some embodiments, when the tube is advanced in a distal direction through the flexible housing 32, the tube may form a fluid path through which blood can be drawn using a blood collection device 60 such as an LLAD or syringe, for example.

In some embodiments, the probe 46 may clear obstructions by one or more of the following: moving the catheter 72 tip; removing thrombus or other obstructions from the catheter 72; extending a new fluid path to a new blood source; holding thrombus at bay; opening one or more valves; and moving the catheter 72 away from an obstruction. In some embodiments, a location and/or position of the probe 46 may be adjusted after initial deployment to facilitate clearing a path for a blood draw. In some embodiments, the probe advancement device 30 may provide tactile and/or auditory feedback to a user to indicate that the initial advancement of the probe 46 is complete.

Referring now to FIG. 1B, a probe advancement system 78 may include a blood collection device 60, the probe advancement device 30, and a catheter assembly 62. In some embodiments, the catheter assembly 62 may include a catheter adapter 64 having a proximal end 68, a distal end 70, and a catheter 72 extending from the distal end 70. In some embodiments, an extension tube 66 may extend from a side port of the catheter adapter 64. FIG. 1B illustrates, according to some embodiments, the probe advancement system 78 just prior to coupling of the probe advancement device 30 to the catheter assembly 62 by insertion of a male luer into the proximal end 68 or a connector 69.

In some embodiments, the probe advancement element 44 may be disposed at the proximal end 36 of the flexible housing 32 and may be coupled to the blood collection device 60. In some embodiments, the probe advancement element 44 may include the probe 46 extending in a distal direction within the flexible housing 32. In some embodiments, the flexible housing 32 may be configured to collapse along the axis 42 in response to the probe 46 being advanced in the distal direction.

Some embodiments of the flexible housing 32 may form a collapsible fluid pathway in fluid communication with the blood collection device 60. In these and other embodiments, blood may flow around the probe 46, which may include a guidewire. In other embodiments, the probe 46 may include a tube, and blood may flow through the tube and not between the tube and an inner surface of the flexible housing 32.

In some embodiments, the probe advancement device 30 may include a connector element 50 disposed within the flexible housing 32 and configured to couple to an end connector 54 at the distal end 38 of the flexible housing 32. In some embodiments, at least a portion of the flexible housing 32 may be transparent such that the probe 46 is visible through an exterior surface 34. In some embodiments, the shaft 81 and/or the probe 46 may be configured to fit through a hole of the connector 50 or may be configured to couple to a corresponding luer of the connector 50. In some embodiments, the connector 50 may include a generally circular disc and/or an extension extending distally from the generally circular disc to the end connector 54, to which the extension may be attached.

As discussed in more detail below, in some embodiments, the near access grip element 52 may be disposed within the flexible housing 32 proximate to the distal end 38. In some embodiments, the near access grip element 52 may be secured to the extension of the connector element 50. Some embodiments of the near access grip element 52 may be configured to manipulate a position of the probe 46 within the flexible housing 32.

In some embodiments, a biasing member 56, such as, for example, a spring, may extend between the connector element 50 and the proximal end 36 such that the probe 46 is biased in a retracted position. In some embodiments, the biasing member 56 may be compressed when the probe 46 is advanced distally. In some embodiments, the biasing member 56 may be configured to automatically retract the probe 46 in the proximal direction.

In some embodiments, the catheter assembly 62 may be coupled to the distal end 38 of the flexible housing 32. In some embodiments, the catheter assembly 62 may be coupled to the probe advancement device 30 and in fluid communication with the collapsible fluid pathway and/or a fluid pathway through the probe 46. In some embodiments, the catheter assembly 62 may be configured to receive the probe 46 therethrough.

Figure 2A:
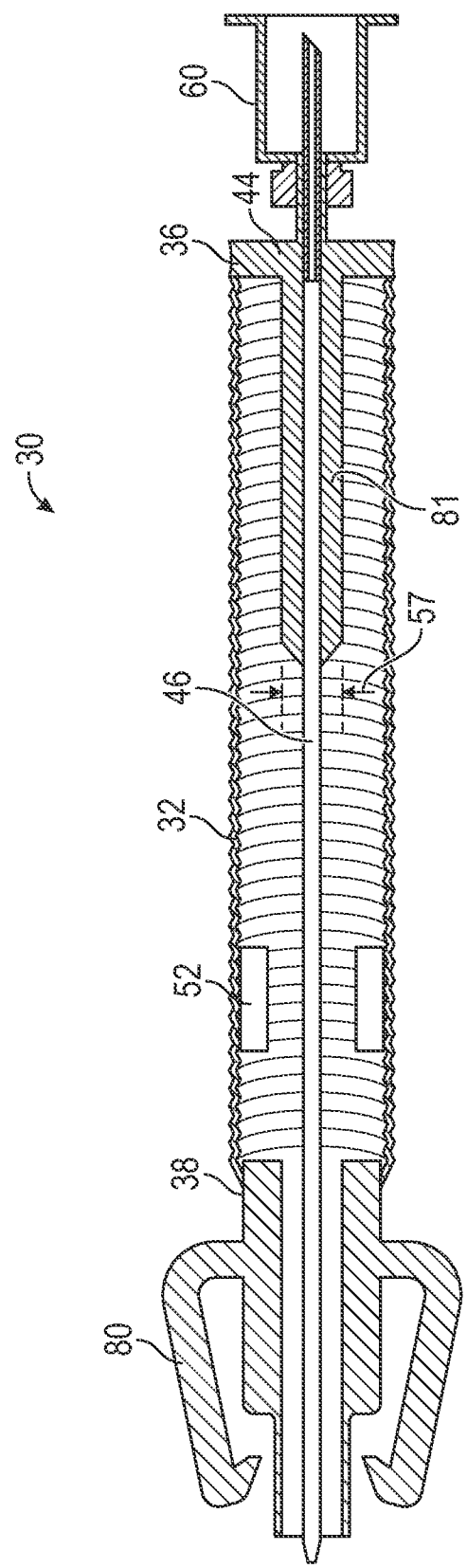
FIG. 2A is a cross-sectional view of another example probe advancement device, illustrating an example probe including a tube, in accordance with some embodiments.
Figure 2B:
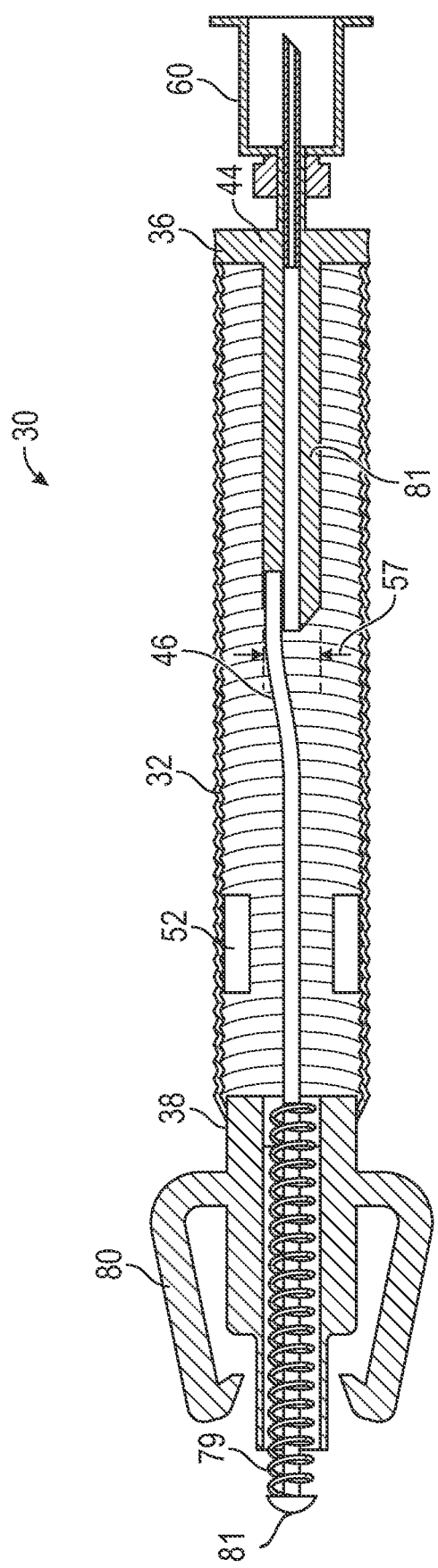
FIG. 2B is a cross-sectional view of another example probe advancement device, illustrating an example probe including a guidewire, in accordance with some embodiments.

Referring now to FIGS. 2A-2B, in some embodiments, advancement of the probe 46 may be accomplished by gripping the proximal end 36 of the probe advancement device 30 and moving the probe 46 distally toward and/or through the catheter 72. In some embodiments, the proximal end 36 of the probe advancement device 30 may include a shape and/or texture to facilitate gripping the proximal end 36 to maneuver a position of the probe 46. It is understood that, in some embodiments, one or more features of FIG. 2 may be combined with one or more features of FIG. 1A and/or FIG. 1B. FIG. 2A illustrates the probe 46 as a tube, according to some embodiments. In some embodiments, the tube may be secured within the shaft 81 in a fluid-tight manner, such as via adhesive or another suitable method. FIG. 2B illustrates the probe 46 as a guidewire, which may be secured to the shaft 81 via adhesive or another suitable method. In some embodiments, the guidewire may be embedded in the shaft 81. In some embodiments, the guidewire may include various shapes to facilitate thrombus removal. In some embodiments, the guidewire may include a straight portion and/or a spiral portion 79. In some embodiments, a distal end of the guidewire may include a blunt element 81, which may include a ball, rounded surface, or another blunt element to avoid damage to the vein.

In some embodiments, the probe 46 may be moved in a distal direction through a catheter assembly and into the vasculature or vein of the patient. In some embodiments, the proximal end 36 of the probe advancement device 30 may be turned or its orientation may be otherwise adjusted to facilitate the flexible housing 32 to facilitate the probe 46 to further advancing in the distal direction. In some embodiments, the probe 46 may be advanced in the distal direction until it is extended through the catheter 72 (see, for example, FIG. 1B).

In some embodiments, the probe 46 may encounter an obstacle that inhibits advancement, such as a thrombus formed inside the tip of the catheter 72 or an S-curve in the catheter 72 resulting when the catheter 72 is plunged into the skin. In these embodiments, a near access grip element 52 located near the distal end 38 may be used to support and advance the probe 46. In some embodiments, the near access grip element 52 may facilitate the probe 46 to be maneuvered more easily by providing a reduced buckling column length.

Indeed, in some embodiments, the probe 46 may have a small moment of inertia when it passes through the catheter 72 or the catheter assembly 62. In some embodiments, while portions of the tube or probe 46 may be well-supported by the catheter assembly 62 in an extended position, other portions may not. As a result, these unsupported portions may buckle when the insertion load is applied.

In this regard, Euler's buckling equation provides:

$$Pcr = \pi^2 EI/L^2$$

where the bending moment of inertia I is equal to $I = \pi r^4/4$ for a solid wire or guidewire, and $I = \pi(Ro^4 - Ri^4)/4$ for a tube. In some embodiments, since the probe 46 must pass through the inside diameter of the catheter 72, the R values may be very small, resulting in a very flexible column which may be prone to buckling. In some embodiments however, shortening a push distance may result in the column being significantly stiffer such that it may support a needed insertion force.

In some embodiments, the near access grip element 52 may include rubber, plastic, metal, or any other suitable material to grip and/or maneuver the probe 46 within the flexible housing 32. In some embodiments, the near access grip element 52 may facilitate translation of the probe 46. In some embodiments, the near access grip element 52 may include exterior features that may be felt and/or manipulated by the user through the flexible housing 32. In some embodiments, the near access grip element 52 may further include one or more surfaces configured to interface with or engage the probe 46. For example, in some embodiments, the surface may include one or more grooves, indentations, or other texture or material to facilitate a secure interface between the near access grip element 52 and the probe 46.

In some embodiments, a user may manipulate the near access grip element 52 to grasp at least a portion of a length of the probe 46. In some embodiments, the user may move the near access grip element 52 to move the probe 46. In some embodiments, near access grip element 52 may be translated or moved along the axis 42 to advance or retract the probe 46 within the catheter 72. In some embodiments, the user may manipulate the near access grip element 52 simultaneously with the proximal end 36 of the flexible housing 32 to move the probe 46 towards and/or through the catheter 72.

In some embodiments, the end connector 54 may include an adapter 80, which may include a female luer adapter on a proximal side and/or a male luer adapter on a distal side. In some embodiments, the proximal end 36 of the probe advancement device 30 may include a luer adapter, such as, for example, a male luer as illustrated in FIG. 2, which may include a width 57. In some embodiments, in response to advancement of the probe 46 distally and collapse of the flexible housing 32, the male luer may be configured to insert into the female luer of the end connector 54 such that the male luer seals the end connector 54. In some embodiments, a width or shape of the female luer may receive the width or shape of the male luer. In some embodiments, male luer may contact an inner surface of the adapter 80 to form a seal, which may reduce or prevent fluid flow through the adapter 80 when the probe 46 is advanced distally and the flexible housing 32 is collapsed. In some embodiments, the flexible housing 32 may be compressed or fully compressed by coupling the male luer to the female luer. In some embodiments, the probe advancement device 30 may not include a septum, which may reduce drag on the probe 46. In other embodiments, the probe advancement device 30 may include a septum.

In some embodiments, a method to advance a probe 46 for a blood draw may include coupling a probe advancement device 30 (see, for example, FIGS. 1-7) to a catheter assembly 62 (see for example, FIG. 2B). In some embodiments, the catheter assembly 62 may include the catheter adapter 64 having the proximal end 68, the distal end 70, and the catheter 72 extending from the distal end 70.

Some embodiments of the probe advancement device 30 may include the flexible housing 32 and the probe advancement element 44. In some embodiments, the flexible housing 32 may include the proximal end 36 and the distal end 38. In some embodiments, the flexible housing 32 may form the collapsible fluid pathway between the proximal end 36 and the distal end 38 and/or around the probe 46, which may include a guidewire. In other embodiments, as illustrated in FIG. 2, a fluid pathway may extend through the probe 46, which may include a tube. In these embodiments, the fluid pathway may not extend between the tube and the flexible housing 32.

In some embodiments, the probe advancement element 44 may be coupled to the proximal end 36 of the flexible housing 32. Some embodiments of the probe advancement device 30 may include the probe 46 extending in a distal direction within the flexible housing 32. In some embodiments, the flexible housing 32 may be configured to collapse along the axis 42 in response to the probe 46 being advanced in the distal direction.

In some embodiments, the method may include coupling the blood collection device 60 to the probe advancement device 30. In some embodiments, the probe 46 may be translated in the distal direction to create a fluid path through the catheter assembly 62. Finally, in some embodiments, the blood collection device 60 may be actuated to collect blood from a patient via the fluid path.

Figure 3:
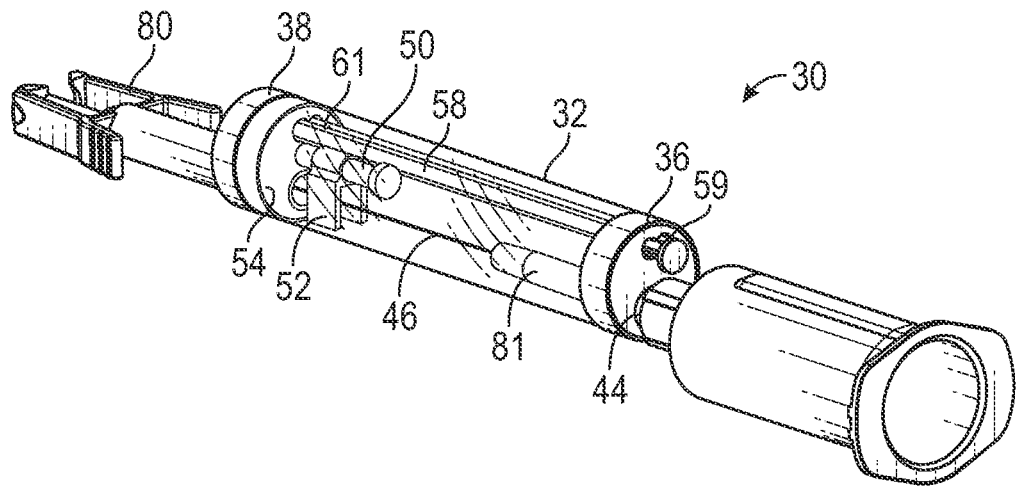
FIG. 3 is a perspective view of another example probe advancement device in accordance with some embodiments.

Referring now to FIG. 3, in some embodiments, an alignment mechanism 58 may be disposed within the flexible housing 32 to maintain alignment between the proximal end 36 and the distal end 38 of the flexible housing 32. In some embodiments, a first end 59 of the alignment mechanism 58 may be slidably coupled to the probe advancement element 44. In some embodiments, a second end 61 of the alignment mechanism 58 may be coupled to the end connector 54. In some embodiments, the end connector 54 may include the adapter 80 or may be coupled to the adapter 80 to create a fluid path between the probe advancement device 30 and the catheter assembly 62 or another device. In some embodiments, the adapter 80 may include a male luer or another suitable adapter.

As illustrated, in some embodiments, the alignment mechanism 58 may include a rigid or resilient rod or other suitable structure extending along or parallel to the axis 42 between the probe advancement element 44 and the end connector 54. In this manner, in some embodiments, the probe advancement element 44 may slide in a distal direction along the alignment mechanism 58 as the flexible housing 32 is compressed to advance the probe 46. Similarly, in some embodiments, the probe advancement element 44 may slide in a proximal direction along the alignment mechanism 58 as the probe 46 is retracted.

Figure 4:
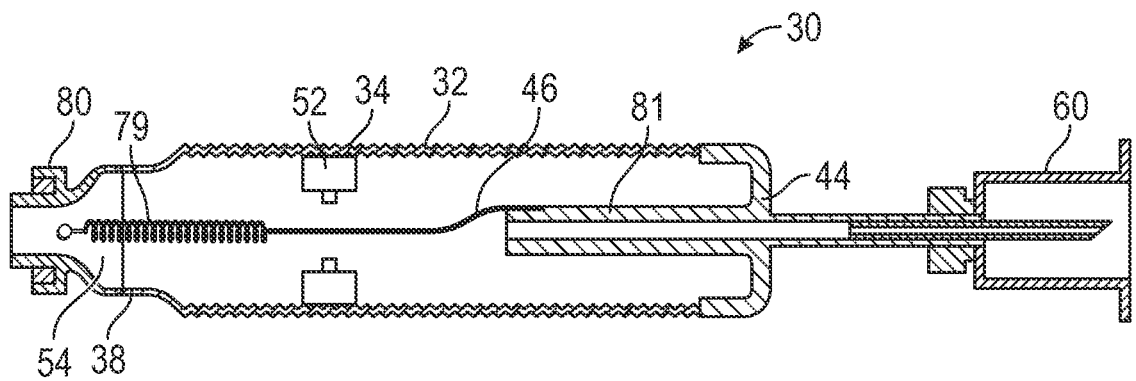
FIG. 4 is a cross-sectional view of another probe advancement device configured in accordance with some embodiments.

Referring now to FIG. 4, in some embodiments, the probe 46 may include a guidewire that may include various shapes to facilitate thrombus removal. In some embodiments, the guidewire may include a straight portion and/or a spiral portion. In some embodiments, a distal end of the guidewire may include a ball or another blunt element to avoid damage to the vein.

In some embodiments, the near access grip element 52 may include a pinching element, which may be configured to pinch the probe 46 similar to a clothes pin or another pinching mechanism. In some embodiments, opposing sides of the pinching element may be brought together by the user to pinch the probe 46, which may facilitate advancement of the probe 46 when its path is impeded.

In some embodiments, a shaft 81 of the male luer of the probe advancement element 44 may be long enough to reach from the near access grip element 52 (with the flexible housing 32 compressed) to an inside of the adapter 80, to seal the probe advancement device 30. In some embodiments, a space between the opposing sides of the pinching element may be large enough to allow the shaft 81 to pass through or greater than a width of the shaft 81. In some embodiments, blood may flow proximally through the probe advancement device 30 and proximally through the shaft 81 for collection. In some embodiments, the probe 46, which may include a guidewire, may extend from the shaft 81 and/or may be bent to align with a longitudinal axis of the probe advancement device 30.

Figure 5:
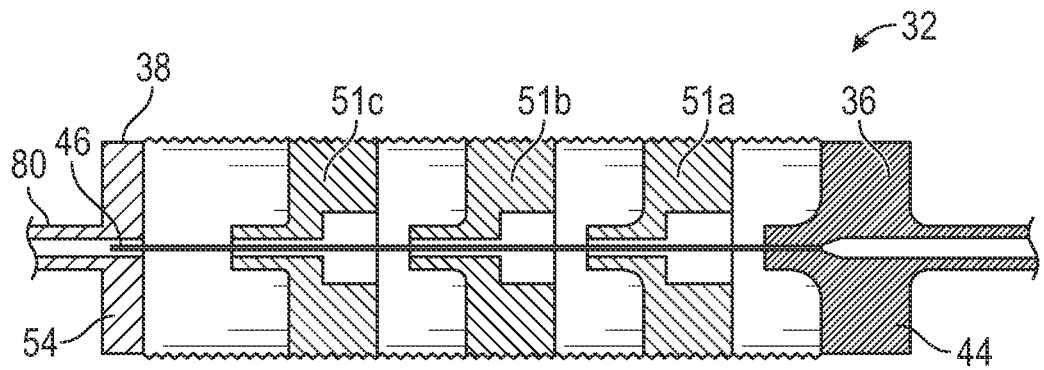
FIG. 5 is a cross-sectional side view of an example support elements disposed within an example flexible housing in accordance with some embodiments.

Referring now to FIG. 5, in some embodiments, the probe advancement device 30 may include a one or more support elements 51*a*-*c* (which may be referred to collectively in the present disclosure as "support elements 51"), which may be disposed within the flexible housing 32 between the proximal end 36 and the end connector 54 at the distal end 38. In some embodiments, each of the support elements 51 may include mating and sealing luers. In further detail, in some embodiments, a distal end of each of the support elements 51 may include a male luer and a proximal end of each of the support elements 51 may include a female luer. In some embodiments, the support elements 51 may thus be configured to couple together. In some embodiments, the distal end of a first of the support elements 51 may couple to a proximal end of a second of the support elements 51 immediately distal to the first of the support elements 51. In some embodiments, the proximal end of the first of the support elements 51 may couple to a distal end of a third of the support elements 51 immediately proximal to the first of the support elements 51. In some embodiments, the probe 46 may extend through the support elements 51, which may support the probe 46 and reduce buckling during advancement of the probe 46 in the distal direction.

In some embodiments, each of the support elements 51 may be configured to lock and unlock. In some embodiments, the support elements 51 may be configured to lock in response to pinching by the user similar to the near access grip element 52. In some embodiments, when a particular support element 51 is locked, the particular support elements 51 may pinch the probe 46 such that movement of the particular support element 51 moves the probe 46. In some embodiments, when the particular support element 51 is unlocked, the particular support element 51 may not pinch the probe 46 and may allow the probe 46 to slide through the particular support element 51. In some embodiments, the third of the support elements 51 may be locked and advanced distally to and/or coupled to the first of the support elements 51, which may be unlocked. In some embodiments, the first of the support elements 51 may then be locked and the third of the support elements 51 may be unlocked, followed by advancement of the first of the support elements 51 and the probe 46 distally. In some embodiments, the first of the support elements 51 may be advanced distally to the second of the support elements 51 and/or may be coupled together with the second of the support elements 51. In some embodiments, the first of the support elements 51 may then be unlocked and the second of the support elements 51 may be locked, followed by advancement of the second of the support elements 51 and the probe 46 distally. In some embodiments, the support elements 51 may facilitate advancement of the probe 46 when the probe 46 encounters an obstacle that inhibits advancement.

In some embodiments, the support elements 51 may provide several advantages, including supporting the probe 46 at various points along a length of the probe 46, which may reduce buckling during advancement of the probe 46. Also, in some embodiments, the support elements 51 between the distal end 38 and the proximal end 36 may reduce blood flowing through the flexible housing 32. In some embodiments, because it may be difficult for blood to pass through the support elements 51, fewer (or no) septa may be disposed within the adapter 80, which may reduce drag on the probe 46 as the probe 46 is advanced. In some instances, drag created by septa may increase a likelihood of buckling of the probe 46.

Figure 6A:
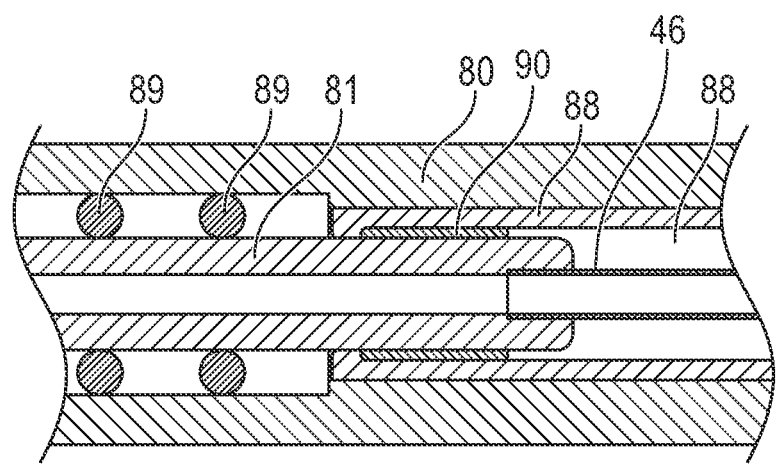
FIG. 6A is a cross-sectional view of one example of a septum disposed within an example adapter in accordance with some embodiments.
Figure 6B:
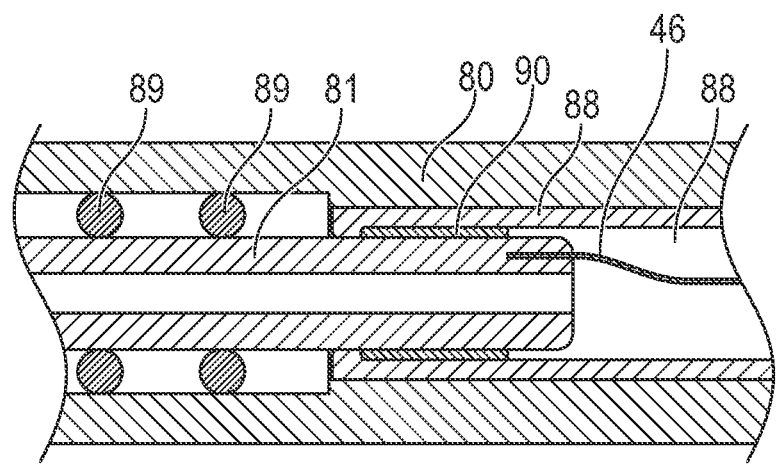
FIG. 6B is a cross-sectional view of the septum of FIG. 6A illustrating another example probe, in accordance with some embodiments.
Figure 6C:
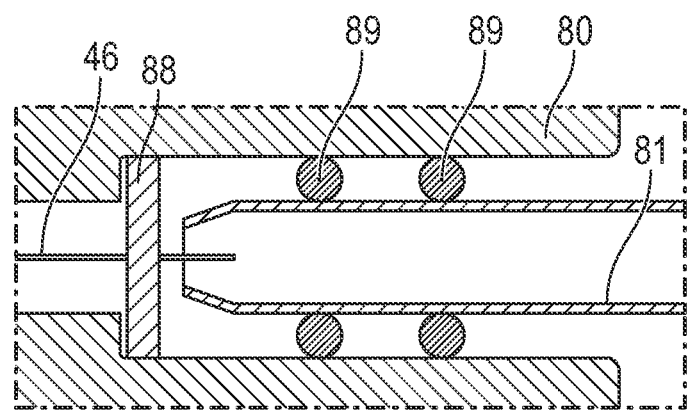
FIG. 6C is a cross-sectional view of another example of a septum disposed within the adapter in accordance with some embodiments.

Referring now to FIGS. 6A, 6B, and 6C, in some embodiments, a septum 88 (or multiple septa 88) may be disposed within the adapter 80. In some embodiments, the septum 88 may facilitate adjustment of the probe 46 after initial placement into or through the catheter 72 (see, for example, FIG. 1B). As illustrated in FIG. 6A, in some embodiments, in response to collapse of the flexible housing 32 and movement of the probe 46 in the distal direction, the shaft 81 and/or the probe 46 may be moved through the septum 88. FIG. 6A illustrates the probe 46 moving distally through the septum 88, according to some embodiments.

In some embodiments, the probe 46 may include a tube, as illustrated, for example in FIG. 6A, and may be configured to draw blood when extended through the catheter 72. In some embodiments, the probe 46 may include a guidewire, as illustrated, for example in FIG. 6B, and may extend from and/or be embedded in the shaft 81.

As illustrated in FIG. 6C, in some embodiments, in response to collapse of the flexible housing 32 and movement of the probe 46 in the distal direction, the probe 46, which may include a guidewire, may be moved through the septum 88. In these and other embodiments, the probe 46 may be embedded in the shaft 81 and/or may be off-center. Thus, in some embodiments, the septum 88 may include a slit that is off-center.

In some embodiments, one or more O-rings 89 may be disposed within the adapter 80 and/or proximal to the septum 88. In some embodiments, the O-rings 89 and/or an elastomeric region 90 of the septum 88 may facilitate movement of the probe 46 between a number of different axial positions while also facilitating support of the probe 46 and fluid sealing. In some embodiments, the O-rings and the elastomeric region 90 may form a seal around the tube or the shaft 81.

In some embodiments, the septum 88 may prevent blood from flowing into a lumen encased by the flexible housing 32 previous to and during advancement of the probe 46. In some embodiments, the septum 88 may also prevent blood from flowing into the lumen encased by the flexible housing 32 during dwell of the catheter 72 with the probe 46 extending therethrough and/or during retraction of the probe 46. In some embodiments, the septum 88 may provide a seal between the shaft 81 and the adapter 38, which may facilitate application of suction for blood collection when the probe 46 is a guidewire. In some embodiments, the seal between the shaft 81 and the adapter 38 provided by the septum 88 may create enough of a hold to allow the user to let go of the proximal end 36 while the user draws blood via the blood collection device 60 and adjust a position of the probe 46, such as via axial advancement. In some embodiments, if there is an obstruction of a fluid pathway flowing into the probe 46 or tube, adjusting the position of the probe 46 may open up the fluid pathway and facilitate blood flow through the probe 46 and/or into the blood collection device 60.

Figure 6D:
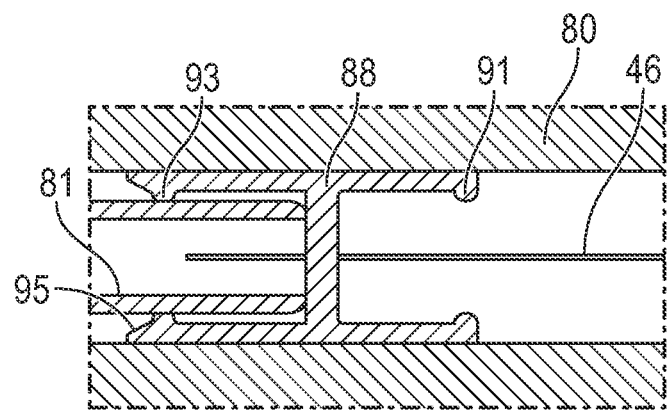
FIG. 6D is cross-sectional view of another example of a septum disposed within the adapter in accordance with some embodiments.
Figure 6E:
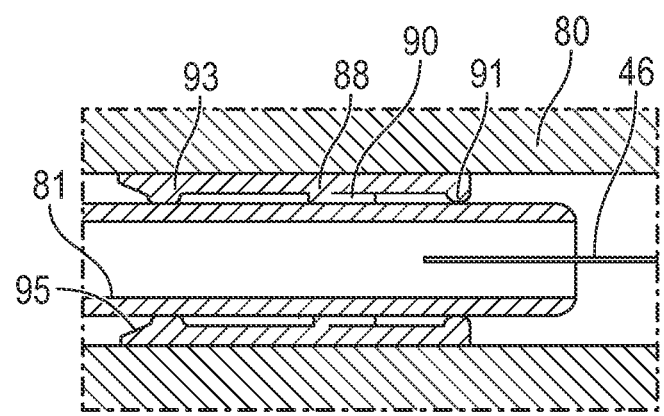
FIG. 6E is cross-sectional view of the septum of FIG. 6D, illustrating an example probe advanced through the septum, in accordance with some embodiments.
Figure 7A:
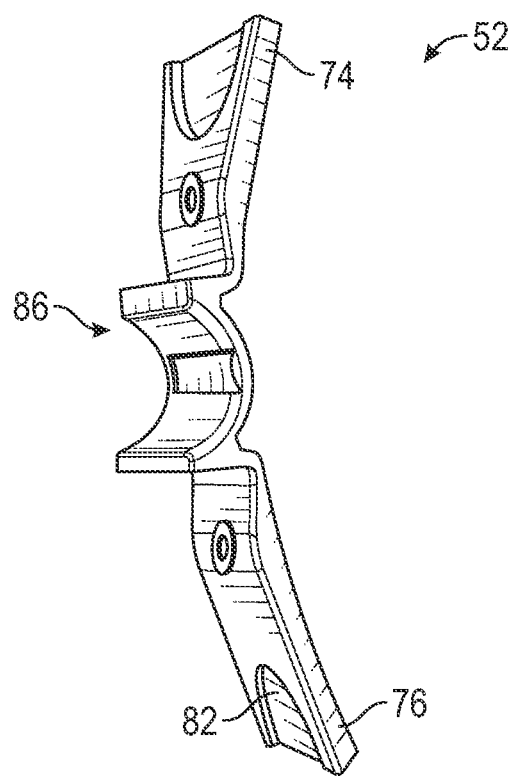
FIG. 7A is an upper perspective view of a near access grip element in accordance with some embodiments.
Figure 7B:
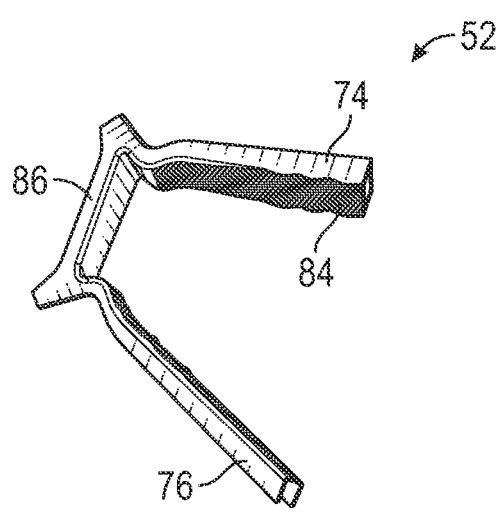
FIG. 7B is a side view of the near access grip element of FIG. 7A.
Figure 7C:
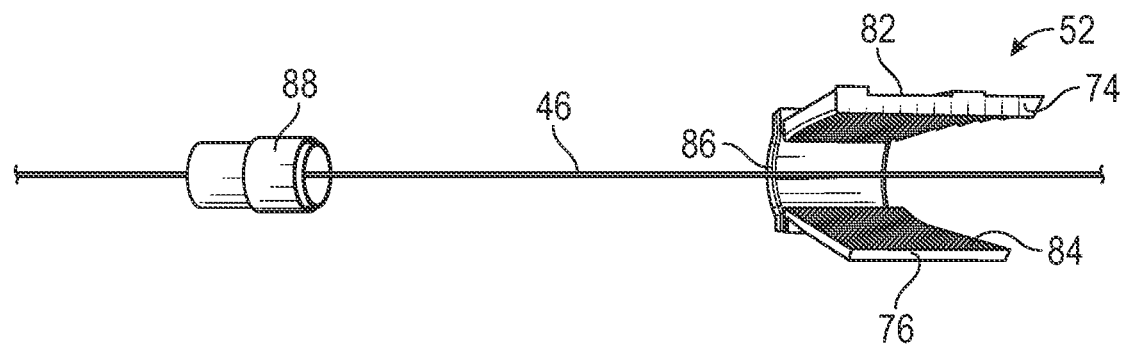
FIG. 7C is a perspective view of the near access grip element of FIG. 7A and an example probe in accordance with some embodiments.
Figure 7D:
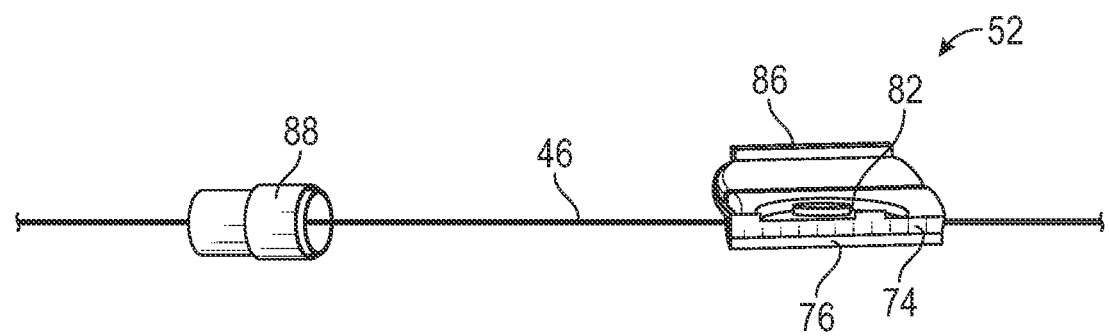
FIG. 7D is a perspective view of the near access grip element of FIG. 7A actuated to grip the probe in accordance with some embodiments.
Figure 7E:
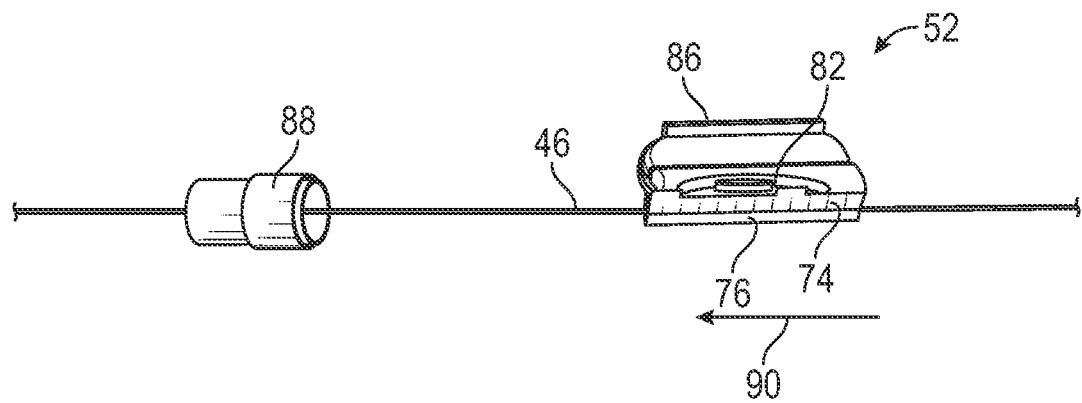
FIG. 7E is a perspective view of the near access grip element of FIG. 7A actuated to translate the probe through an example septum in accordance with some embodiments.

As illustrated in FIGS. 6A-6E, a shape of the septum 88 may vary. Referring now to FIGS. 6D-6E, an inner surface of the septum 88 may include bumps 91 and/or other bumps 93, which may provide a similar function as the O-rings 89 and the elastomeric region 90. In further detail, the bumps 91 and/or the other bumps 93 may form a seal around the probe 46 or the shaft 81 and/or may support the probe 46 or the shaft 81. In some embodiments, the bumps 91 may be on one side of a folded portion of the septum and the other bumps 93 may be on an opposite side of the folded portion. In some embodiments, the folded portion may perform a same or similar function as the elastomeric region 90 and may provide a seal around the shaft 81. In some embodiments, a proximal end of the septum 88 may include a lead-in or tapered portion 95 to facilitate guidance of the probe 46. In some embodiments, the septum 88 may include an H-shape cross-section and a middle portion of the H-shape cross-section and septum 88 may open in response to the shaft 81 and/or the probe 46 moving through the septum 88, as illustrated in FIGS. 6D-6E. In these embodiments, the middle portion may fold towards the elastomeric region 90.

Referring now to FIGS. 7A-7E, in some embodiments, the near access grip element 52 may include a resilient material having a hinge 86 such that the near access grip element 52 may be configured to grasp or pinch the probe 46 between a first end 74 and a second end 76. In some embodiments, the hinge 86 may be formed to have a spring tendency to maintain the first end 74 and the second end 76 in an open position. In some embodiments, the near access grip element 52 may include a biasing mechanism integrated therewith or coupled thereto to maintain the open position between the first end 74 and the second end 76. In some embodiments, the near access grip element 52 may be visible through the flexible housing 32 and may include a size and a shape to facilitate visualizing and/or manipulating the near access grip element 52 through the flexible housing 32.

In some embodiments, in the event advancement of the probe 46 is impeded, the near access grip element 52 may be actuated to grip the probe 46. In some embodiments, the near access grip element 52 and probe 46 may be manually translated in a distal direction to move the probe 46 to overcome or bypass the obstacle. In some embodiments, the probe advancement element 44 and/or the near access grip element 52 may further advance the probe 46 after passing or otherwise overcoming the obstacle. In some embodiments, the probe advancement element 44 and/or the near access grip element 52 may also be utilized to retract the probe 46 in the proximal direction within the flexible housing 32.

It is understood that embodiments of one or more of FIGS. 1-7 may be combined. For example, the probe advancement device 30 of FIG. 1A may be similar or identical to the probe advancement device 30 of FIG. 1B in terms of one or more features and/or operation. As another example, the probe advancement device 30 of FIG. 1A may be similar or identical to the probe advancement device 30 of FIG. 2 in terms of one or more features and/or operation. As a further example, the probe advancement device 30 of FIG. 3 may be similar or identical to the probe advancement device 30 of FIG. 4 in terms of one or more features and/or operation.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A probe advancement device configured to couple to a catheter assembly, the probe advancement device comprising:
   a flexible housing comprising a proximal end and a distal end;
   a probe advancement element coupled to the proximal end of the flexible housing, the probe advancement element comprising a probe extending in a distal direction within the flexible housing, wherein the flexible housing is configured to collapse along an axis in response to the probe being advanced in the distal direction; and
   at least one support element disposed within the flexible housing,
   wherein the probe extends through the at least one support element, and
   wherein a distal end of the at least one support element comprises a male luer and a proximal end of the at least one support element comprises a female luer.

2. The probe advancement device of claim 1, wherein the probe comprises one of a guidewire and a tube.

3. The probe advancement device of claim 1, wherein a proximal end of the probe advancement element is configured to couple to a blood collection device.

4. The probe advancement device of claim 1, wherein the at least one support element comprises a plurality of support elements spaced apart within the flexible housing, wherein the probe extends through the plurality of support elements, wherein a distal end of each of the support elements comprises a male luer and a proximal end of each of the support elements comprises a female luer, wherein the plurality of support elements decrease an amount of blood flowing proximally through the flexible housing.

5. The probe advancement device of claim 4, wherein each of the plurality of support elements is configured to lock on the probe.

6. The probe advancement device of claim 1, further comprising an adapter disposed at the distal end of the flexible housing and configured to couple to a catheter assembly, wherein no septa are disposed within the adapter.

7. The probe advancement device of claim 1, further comprising an end connector disposed at the distal end of the flexible housing a second connector disposed at the proximal end of the flexible housing, wherein in response to the probe being advanced in the distal direction and collapse of the flexible housing, the end connector is configured to couple to the second connector.

8. The probe advancement device of claim 7, wherein the end connector comprises a female luer adapter and the second connector comprises a male luer adapter.

9. The probe advancement device of claim 7, further comprising an alignment rod disposed within the flexible housing to maintain alignment between the probe advancement element and the end connector.

10. The probe advancement device of claim 1, wherein at least a portion of the flexible housing is transparent such that the probe is visible through the flexible housing.

11. The probe advancement device of claim 1, further comprising a biasing member disposed within the flexible housing between the probe advancement element and the distal end of the flexible housing, wherein the biasing member is configured to bias the probe in a retracted position.

12. The probe advancement device of claim 11, wherein the probe advancement element is configured to compress the biasing member in the distal direction to collapse the flexible housing along the axis in response to the probe being advanced in the distal direction.

13. The probe advancement device of claim 1, further comprising a near access grip element disposed within the flexible housing towards the distal end, wherein the near access grip element comprises a first end and a second end configured to be resiliently pinched together such that the probe is retained therebetween.

14. The probe advancement device of claim 13, wherein the near access grip element is configured to be selectively translated along or parallel to the axis within the flexible housing.

15. A probe advancement system, comprising:
   a blood collection device;
   a flexible housing, comprising a proximal end, and a fluid pathway extending therethrough;
   a probe advancement element disposed at the proximal end of the flexible housing and coupled to the blood collection device, the probe advancement element comprising a probe extending in a distal direction within the flexible housing, wherein the fluid pathway is in fluid communication with the blood collection device;
   at least one support element disposed in the flexible housing; and
   a catheter assembly coupled to a distal end of the flexible housing and in fluid communication with the fluid pathway, the catheter assembly configured to receive the probe therethrough,
   wherein the probe extends through the at least one support element, and
   wherein a distal end of the at least one support element comprises a male luer and a proximal end of the at least one support element comprises a female luer.

16. The probe advancement system of claim 15, wherein the fluid pathway is configured to collapse along an axis of the flexible housing in response to the probe being advanced in the distal direction.

17. The probe advancement system of claim 15, wherein the probe comprises a tube, wherein the fluid pathway extends through the tube.

18. The probe advancement system of claim 17, wherein the proximal end of the flexible housing comprises a connector, wherein the connector comprises a shaft, wherein the tube extends distally from the shaft.

19. The probe advancement system of claim 18, wherein the distal end of the flexible housing comprises an end connector, wherein the shaft is configured to insert into the end connector to form a fluid-tight seal.

* * * * *

UNITED STATES PATENT AND TRADEMARK OFFICE
CERTIFICATE OF CORRECTION

PATENT NO. : 12,343,146 B2
APPLICATION NO. : 17/570554
DATED : July 1, 2025
INVENTOR(S) : Curtis H. Blanchard et al.

Page 1 of 1

It is certified that error appears in the above-identified patent and that said Letters Patent is hereby corrected as shown below:

In the Claims

Column 14, Line 5, Claim 7, delete "housing" and insert -- housing and --

Signed and Sealed this
Nineteenth Day of August, 2025

Coke Morgan Stewart
*Acting Director of the United States Patent and Trademark Office*